United States Patent
De Jong et al.

(10) Patent No.: US 9,062,736 B2
(45) Date of Patent: *Jun. 23, 2015

(54) NODAL SPRING ASSEMBLY FOR AN ELECTRONIC TOOTHBRUSH

(71) Applicant: KONINKLIJKE PHILIPS ELECTRONICS N.V., Eindhoven (NL)

(72) Inventors: Gerrit Jan De Jong, Irnsum (NL); Michiel Allan Aurelius Schallig, Drachten (NL); Hendrik Richard Jousma, Groningen (NL); Martinus Bernardus Stapelbroek, Rolde (NL); Tyler G. Kloster, Snoqualmie, WA (US); Scott E. Hall, Issaquah, WA (US); Patrick A. Headstrom, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 42 days.

This patent is subject to a terminal disclaimer.

(21) Appl. No.: 13/858,963

(22) Filed: Apr. 9, 2013

(65) Prior Publication Data
US 2014/0300039 A1    Oct. 9, 2014

(51) Int. Cl.
F16F 1/14    (2006.01)
F16F 1/16    (2006.01)

(52) U.S. Cl.
CPC ........................................ *F16F 1/16* (2013.01)

(58) Field of Classification Search
CPC ..................................... F16F 1/16; F16F 1/14

USPC ......... 267/154, 150, 158, 160, 161, 162, 180, 267/182; 15/22.1, 22.2, 23, 28, 167.1, 15/167.2; 433/118, 131, 216; 403/120, 403/166, 220, 225
See application file for complete search history.

(56) References Cited

U.S. PATENT DOCUMENTS

| | | | |
|---|---|---|---|
| 2,789,812 A | 4/1957 | Ruegg et al. | |
| 4,968,010 A | 11/1990 | Odobasic | |
| 1,378,153 A | 1/1995 | Guiliani et al. | |
| 5,378,153 A * | 1/1995 | Giuliani et al. | ............... 433/216 |
| 5,617,602 A | 4/1997 | Okada | |
| 6,003,189 A | 12/1999 | Falleiros | |
| 6,859,968 B2 | 3/2005 | Miller et al. | |
| 6,997,446 B2 * | 2/2006 | Hall et al. | ...................... 267/154 |
| 8,413,969 B2 * | 4/2013 | De Jong et al. | ............... 267/180 |
| 2003/0204924 A1 | 11/2003 | Grez et al. | |
| 2003/0205858 A1 * | 11/2003 | Hall et al. | ...................... 267/154 |
| 2004/0000016 A1 | 1/2004 | Miller et al. | |
| 2011/0119848 A1 | 5/2011 | Kloster et al. | |

FOREIGN PATENT DOCUMENTS

WO    2005058189 A    6/2005

* cited by examiner

*Primary Examiner* — Pamela Rodriguez

(57) ABSTRACT

A nodally mounted spring arrangement for a drive train which is used in an electronic toothbrush which includes a housing. A V shaped spring member (15) is secured at both ends thereof, wherein the spring member has a node point (30) along a ridge line, approximately halfway along the length of the spring member. A mounting plate (26) member is fixedly connected to the node point of the spring member and also fixedly connected to the housing of the toothbrush.

5 Claims, 5 Drawing Sheets

NODAL SPRING ASSEMBLY FOR AN ELECTRONIC TOOTHBRUSH

This invention relates generally to drive train assemblies for an electronic toothbrush, and more specifically concerns a nodal spring arrangement for such a drive train.

Various drive train arrangements are known for electronic toothbrushes. The drive train portion of the toothbrush is responsive to a motor action, including mechanical, electro-mechanical, magnetic or other action, to drive a brushhead in a reciprocating manner. One type of drive train arrangement uses a spring which is fixedly mounted at both ends as well as at a node point, wherein the node point is between the two ends of the spring, typically mid-length. When the drive action excites the spring in its desired out-of-phase torsion mode, it produces a desired reciprocating brushhead action through a selected angle.

In one arrangement, the nodally mounted torsion spring is V-shaped, having a node point which is connected to the housing by a mounting plate. In such arrangements, the mounting plate, which acts as a ground connection for the V-shaped torsion spring bar, is connected to the handle frame/housing, reducing vibrations which would otherwise be transferred to the handle. The V-shaped torsion bar, which acts as a node spring, has several important functions, including returning the brushhead, or other workpiece, to a center position and to clearly separate the in-phase rotational mode from the desired out-of-phase rotational mode sufficiently to avoid interaction between the two modes. Such a V-spring arrangement is described in U.S. Pat. No. 6,859,986, the contents of which are hereby incorporated by reference. That patent is owned by the assignee of the present invention.

In the above-described nodal spring arrangement, there are several structural challenges to achieving a desired and reliable operation. It is important that the node spring be arranged so that the desired dynamic response of the torsion spring is achieved and to reduce the high stresses and the potential for wear in the area of contact between the V-spring and the mounting plate. It is also important that the response of the V-spring be as linear as possible along the length thereof, as opposed to a non-linear response.

SUMMARY OF THE INVENTION

Accordingly, the nodally mounted spring arrangement for a drive train used in an electronic toothbrush having a housing comprises: a V shaped spring member secured at both ends thereof, the spring member having a node point along the length thereof; and a mounting plate member fixedly connected to the node point of the spring member and fixedly connected to the housing of the toothbrush, wherein in operation the spring member is excited in and out-of-phase mode, such that rotation of one portion of the spring member in one direction results in a rotation of the remaining portion of the spring member in the opposite direction.

Figure 1:
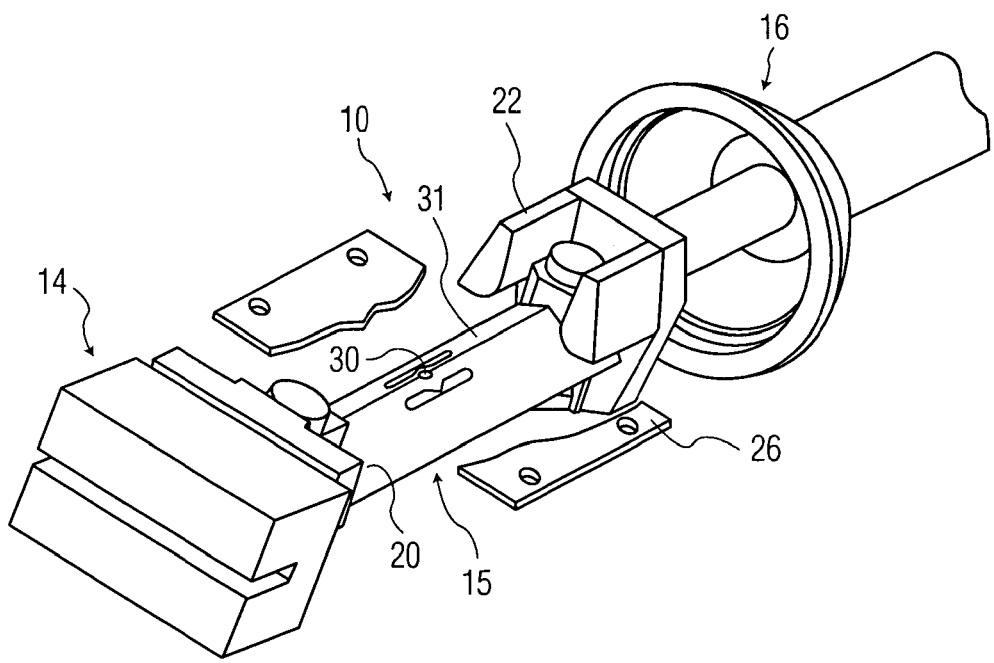
FIG. 1 is a perspective view of a portion of an electronic toothbrush showing a V-spring with an integrated node spring function and mounting plate drive train arrangement for an electronic toothbrush.
Figure 2:
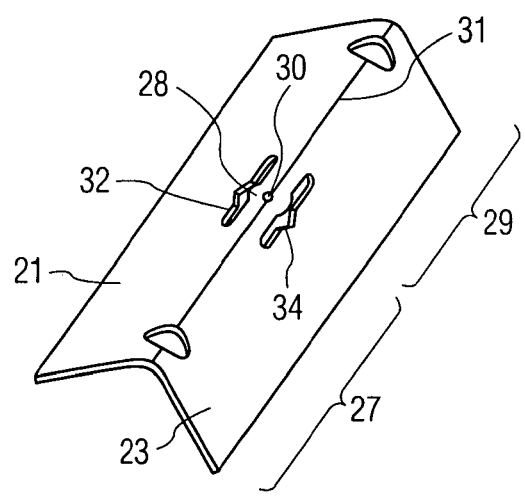
FIG. 2 is a perspective view showing the V-spring portion of the arrangement of FIG. 1 in more detail.

Referring now to FIGS. 1 and 2, a nodal drive train assembly portion of an electronic toothbrush is shown which incorporates one embodiment of the nodal mount assembly disclosed herein. The nodal drive train assembly shown at 10 includes a front end portion 14 of an electromagnetic motor, driving a V-configured torsional bar spring 15. The remainder of the motor is in a handle portion of the toothbrush (not shown). Such an electromagnetic motor arrangement is disclosed in U.S. Pat. No. 5,378,153, which is owned by the assignee of the present invention, the contents of which are hereby incorporated by reference. At the other end of drive train 10 is a portion of a toothbrush head assembly 16. In one arrangement, the entire drive train assembly, including the head assembly, is removable from a handle portion of the toothbrush and replaceable as a unit, while in another arrangement, a brushhead is removable by itself from a mounting member at the distal end 17 of drive train 10.

The V-shaped solid torsion member 15, also referred to as a torsion spring, extends between the two portions 14 and 16 and is fixedly supported by two end mount assemblies 20 and 22, which can be of various configurations. In a particular embodiment, the torsion member 15 is approximately 35 mm long, and comprises two identical plate portions 21 and 23, which are approximately 4.25 mm wide and 0.30 mm thick, made from spring steel. The assembly shown in FIG. 1 is typically supported to the housing of the toothbrush by spaced bearing assemblies (not shown) at the opposing ends thereof. A detailed example of such an arrangement of a nodal mounted drive train is shown and described in the '986 patent.

In operation, the drive motor action excites the torsion bar spring 15 in its out-of-phase mode, such that rotation of the proximal half 27 of the torsion spring in one direction results in a rotation of the distal half 29 in the opposite direction. The frequency of the out-of-phase mode is approximately 270 Hz in the embodiment shown.

In this embodiment, a mounting plate 26 is fixedly connected to the node point 30 of the V-shaped torsion spring by welding or similar fixed connection. The node point is located approximately midway of the V-shaped member, along the ridge line 31 of the V-shaped member. The mounting plate is also connected fixedly to the housing of the toothbrush. This arrangement reduces the vibration of the handle.

In the embodiment of FIGS. 1-2, the stresses typically present at the node joint are reduced by a pair of slots in the V-shaped member. The slots, which result in the V-shaped torsion spring member functioning as a torsion bar node spring, 32 and 34 in the embodiment shown, are substantially identical and are located close to the ridge line, on opposite sides of the node point 28 in the respective plate portions 21, 23 of the V-shaped bar member. The slots 32, 34 extend longitudinally of the V-shaped member and are approximately 8 mm long and 2.4 mm wide. The effect of the slots is to more evenly distribute the stresses along the V-shaped member and reduce the stress in the vicinity of the node point 28, as well as integrating a node spring function into a torsion bar 15. The slots, while generally being uniform in width along their length, may include small tab portions which decrease the slot width at those points.

Figure 3:
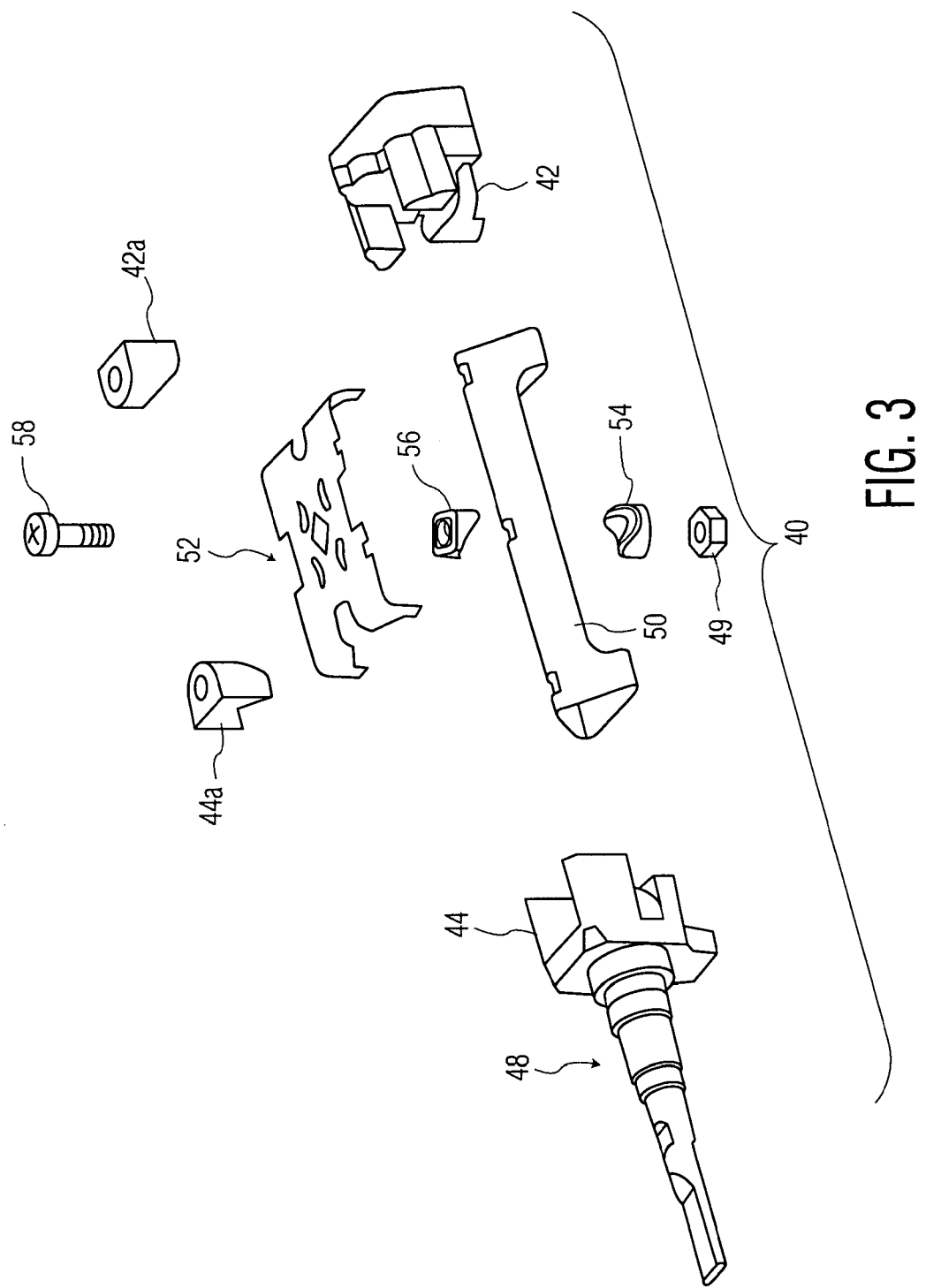
FIG. 3 is an exploded view showing another V-spring and node spring arrangement in an electronic toothbrush.

FIGS. 3-7 show another embodiment of the present invention. FIG. 3 shows a nodal drive train arrangement 40 which includes a V-shaped bar spring member 50 which is fixedly mounted at the respective ends thereof to end mount assembles 42 and 44. End mount assembly 42 is driven by a motor (not shown); extending from end mount 44 is a mount 48 for a brushhead assembly. As with the first embodiment, the entire drive train can be made replaceable relative to a handle portion of a toothbrush, or the structure can be arranged so that the brushhead assembly alone is replaceable.

Extending between support members 42a, 44a, which are mounted in end mount assemblies 42, 44, is a V-shaped torsion member 50, which functions as a spring. Mounted to the center point (node point) 28 of torsion spring 50 is a separate node spring 52, in the form of a mounting plate, unlike the embodiment of FIGS. 1 and 2 in which the nodal spring function is integrated into the V-shaped bar member. The mounting plate (node spring) 52 is fixedly attached to the housing of the toothbrush at its outer edges thereof. In this arrangement, mounting plate 52 is secured to the V-shaped torsion spring 50 (V-spring) by a mounting assembly, which includes generally a base insert member 54 which fits within the trough portion of the V-shaped torsion spring 50, a shim member 56 which is positioned between the torsion spring 50 and the node spring 52, configured to provide a stable connection therebetween, and an attachment member combination 58, 49 which secures the entire assembly firmly together.

There can be several structural variations of the general arrangement shown in FIG. 3. In all of the variations, however, there are several common functions of the assembly. First, the axis of rotation of the node spring (i.e. mounting plate) 52 should be as close as possible to the axis of rotation of the V-spring 50, in order to achieve the desired dynamic response. Second, the mounting assembly, specifically the insert, shim and the attachment member combination, must provide a stable, strong connection between the V-shaped torsion spring and the node spring (mounting plate) at the node point, in such a manner as to withstand the particular stress at the node point connection for an extended period of time, while also reducing the stresses at that point. Third, the joint must be strong and fixed, so that the out-of-phase response of the V-shaped torsion spring is as linear as possible.

Figure 4:
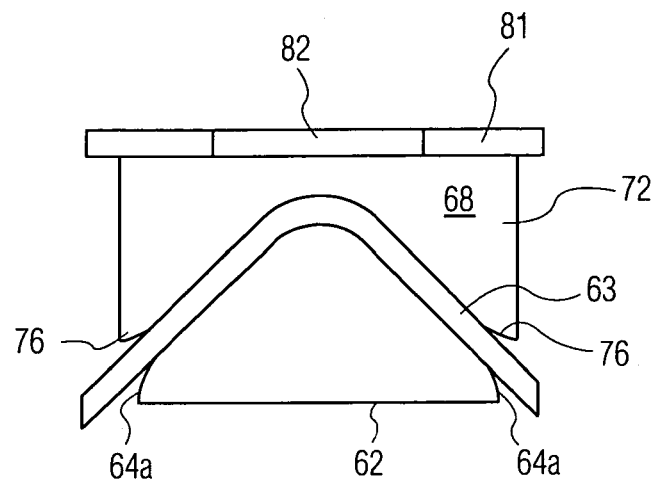
FIG. 4 is a cross-section view showing one variation of the embodiment of FIG. 3 in more detail.
Figure 5:
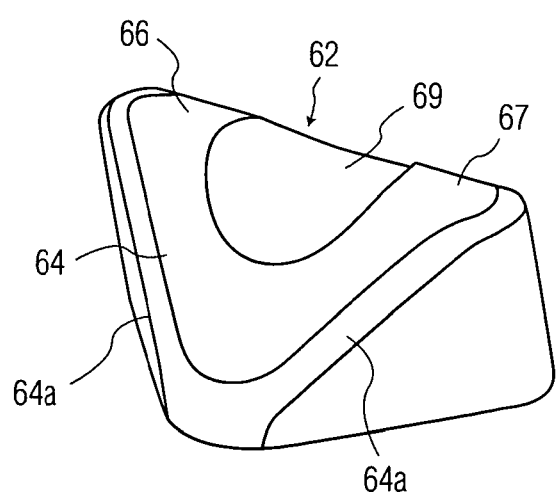
FIG. 5 is a perspective view showing a portion of the variation of FIG. 4 in detail.

In a first variation, shown in FIGS. 4, 5 and 6A, 6B, the insert member 62 is a diamond-shaped assembly. Referring to FIGS. 4 and 5, shoulder (side) portions 64 are flat, configured generally to provide a good extended clamping surface between the insert 62 and the V-spring 63. The edges 64a of the insert round downwardly to avoid stress concentrations. The curve of the upper surface portions 66, 67 is such as to correctly mate the insert relative to the inner surface of the V-spring where the two plate portions thereof meet. The upper surface portions of the insert must have a slightly larger radius than the corresponding internal surface area 68 of the V-shaped torsion spring so that the torsion spring will sit flush on the flat shoulder portions 64 when the assembly is clamped together. An opening 69 extends through the insert member 62 for the attachment member.

Figure 6A:
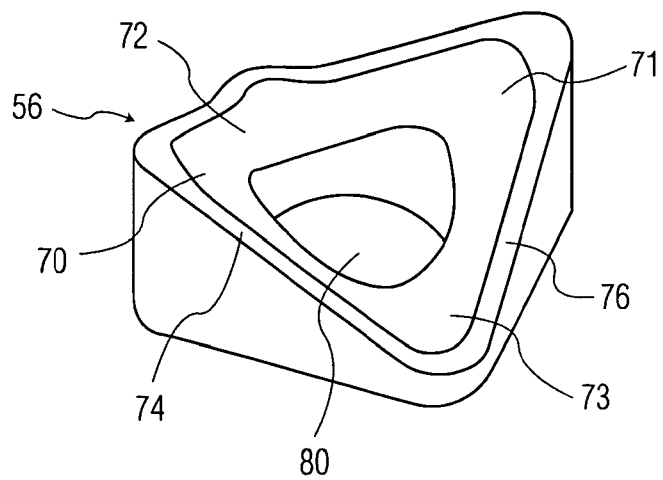
FIGS. 6A and 6B show another portion of the variation of FIG. 4.
Figure 6B:
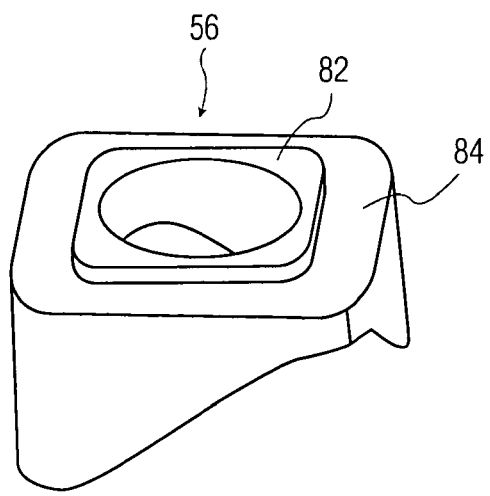

A first shim member 56 for the first variation is shown in FIGS. 6A and 6B. Referring to FIG. 3, shim member 56 is in the general form of a V-shaped block and is configured to fit on the top surface of the V-shaped torsion spring 50, providing a stable clamping surface for the node spring 52. Flat side shoulder portions 70, 71 provide a clamping surface to the V-spring 50, while surface portions 72, 73 mate with the corresponding joint area (the upper surface of the bend) between the two plate portions of the V-spring 63 (FIG. 4). Outer edges 74 and 76 of surfaces 70-73 of the shim curve outwardly, avoiding the stress concentrations. Surface portions 72, 73 have a smaller radius than the radius of the mating surfaces of the V-spring, so that the V-spring will contact flush the flat shoulder surface portions 70, 71 of the shim. An opening 80 through the shim is provided for the attachment member.

The opposing side of the V-block shim 56 includes a raised surface portion 82 which provides a keying function for positioning of the node spring (mounting plate) 81 thereon, while an adjacent flat surface 84 portion provides a clamping surface between node spring 81 and shim 56. The raised surface 82 extends into a mating opening in the node spring 81. The keying function can be accomplished by many different surface configurations, as long as the structure can react the torque loads on the joint.

Both the diamond-shaped insert and the V-block shim are shaped generally to allow the V-spring to deform in a manner as close to its natural state as possible, and to minimize stress increases, while at the same time providing substantial clamping surfaces between the assembly elements. The shim aligns the V-spring to the node spring and sets the gap between the node spring and the V-spring to prevent rubbing movement during operation.

The entire assembly (FIG. 3) is clamped together with a screw and nut combination 58 and 49, but it should be understood that other mechanical attachment means, such as a rivet, can also be used. The clamping surfaces of both the shim and the insert mate with the joining angle of the V-spring and sit flush on that portion of the V-spring, so as to prevent play in the assembly during operation. The actual area of contact between the insert, the V-spring and the shim must be small enough, however, to not significantly affect the overall stiffness of the V-spring member, but still great enough to provide an adequate clamping surface that the assembly lasts for the desired life of the product.

The insert and the shim portions of the node assembly should comprise a bearing-type material with a low friction, less than that of the V-spring, which is typically made from steel, in order to avoid wear between the V-spring, the insert and the shim, and to maintain a gradual stress introduction zone in the V-spring. Furthermore, the material must have a high enough yield strength to strongly hold the attachment member (rivet or screw), and yet must resist wear and loosening of the joint over the life of the product. Brass and bronze have shown to fulfill these requirements. Both have good bearing properties and high yield strength. Other materials, such as aluminum and zinc, could also be used.

The entire node assembly must be clamped tightly to maintain a tight joint therebetween, without play or movement between them, for the desired life of the product. The overall geometry of the insert and the shim minimize the clamping pressure produced by the approximately 500 N clamping force required to produce the desired tight arrangement, while the particular material of the insert and the shim creates a good friction/high wear tolerance surface between the V-spring, shim and insert elements.

A variation of the second embodiment includes different insert and shim configurations, shown in FIGS. 7A, 7B and 8A, 8B, which provide the required clamping surfaces for attachment and alignment of the V-spring member, with different insert and shim configurations, which also provide a low friction bearing surface between the V-spring and the node spring (mounting plate).

Figure 7:
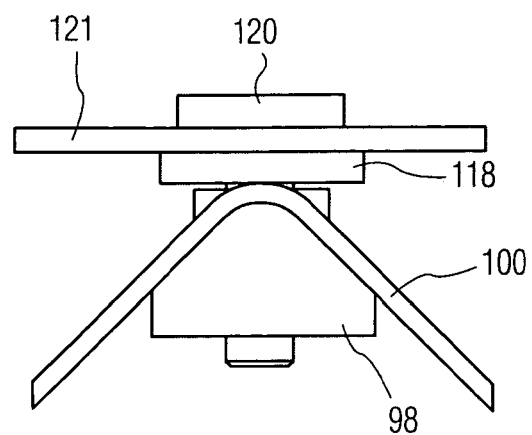
FIG. 7 is an elevational view of another variation of the embodiment of FIG. 3.

Referring now to FIG. 7, insert 98 is round in general configuration and includes opposing flat side shoulder surfaces 104 and 105, which provide the required clamping surfaces between insert 98 and the V-spring 100, and positions the insert correctly relative to the V-spring. Again, the outer edges 106 of the flat side shoulder surfaces are rounded to avoid stress concentrations. The insert 98 also includes an upper raised portion 108 which functions as a keying element, extending upward through an opening in the V-spring. Upper surface portions 107 of the insert have a slightly larger radius than the lower surface of the V-spring member and the joint thereof, so that the V-spring will sit flush on the flat shoulder portions of the insert when the assembly is clamped together.

Intermediate between the keying portion 108 and the flat shoulder surfaces 104, 105 is a bearing boss 109 which provides a bearing surface for the node opening in the V-spring. The height of the bearing boss 109 must not interfere with the clamping action for the assembly, but is designed for an interference fit with an opening in the V-spring.

A groove 116 between the bearing boss 109 and the flat shoulder surfaces 104, 105 of the insert allows the V-spring to sit flush on those flat shoulder portions. The keying element 108 is configured to provide a slight interference fit with the corresponding opening in the V-spring. Opening 110 through element 108 is adapted to receive an attachment member therethrough. The base surface 111 of insert 108 provides support for a nut in the case of a screw and nut assembly or a clamping surface for the deformed end of a rivet connector.

A flat shim portion 118 is circular, with a diameter of approximately 4 mm, approximately 0.5 mm thick, with a central opening 122 which matches the raised keying portion 108 of the insert. The flat shim supports the mounting plate 121, as shown in FIG. 7. An attachment member 120 secures the existing assembly together firmly.

The above two variations can be in turn varied. For instance, the bearing boss portion of the insert of FIG. 8A can be used with the insert of FIG. 4 for an interference fit with an opening in the V-spring.

Figure 8A:
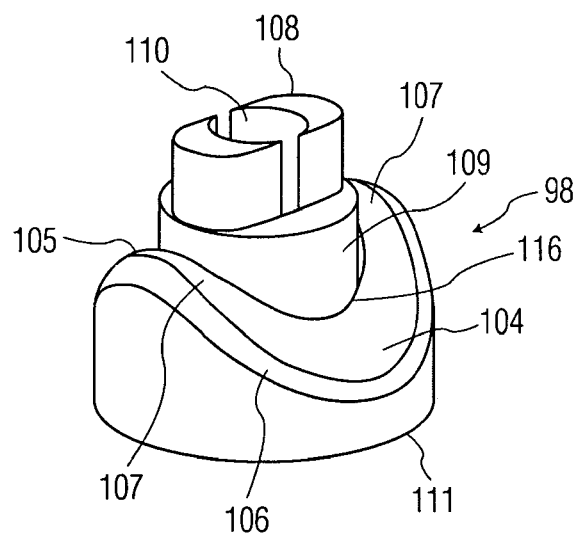
FIGS. 8A and 8B are perspective views of portions of the variation of FIGS. 7A and 7B.
Figure 8B:
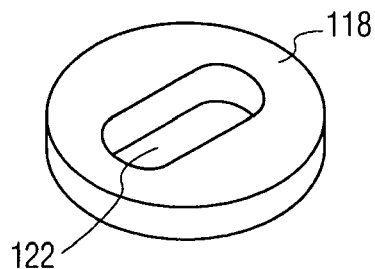

In a further variation, the arrangement of FIGS. 7, 8A, 8B can be modified so that the shim of FIG. 8B is replaced with the shim of FIGS. 6A, 6B; and still further, the insert of FIG. 8A can be modified to eliminate the bearing boss and then used with the shim of FIGS. 6A, 6B.

Still further, the insert of FIG. 5 can be used with the shim of FIG. 8B, and in yet another variation, the insert of FIG. 5 can be modified to include a bearing boss portion and used with the shim of FIG. 8B.

Hence, a nodal spring arrangement has been described in which a V-shaped torsion member (spring) is secured at its node point to the handle housing by a mounting plate. In one embodiment, the mounting plate is welded to the V-shaped spring at the node point; slots provided in the V-shaped spring are located on opposing sides of the node point. These slots create a torsion bar node spring while also reducing stresses around the node point connection zone. Another embodiment includes a node point assembly which includes an insert supporting the V-shaped torsion spring and a shim member located between the V-shaped torsion spring and the mounting plate node spring, the assembly being held tightly together by an attachment member combination, such as a screw or a rivet.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A nodally mounted spring arrangement for a drive train used in an electronic toothbrush having a housing, comprising:
    a V shaped spring member secured (15) at both ends thereof, the spring member having a node point (30) along the length thereof; and
    a mounting plate member (26) fixedly connected to the node point of the spring member and fixedly connected to the housing of the toothbrush, wherein in operation the spring member is excited in an out-of-phase mode, such that rotation of one portion of the spring member in one direction results in a rotation of the remaining portion of the spring member in the opposite direction.

2. The spring arrangement of claim 1, wherein a proximal half (27) of the spring member rotates in one direction while a distal half (29) thereof rotates in the opposite direction.

3. The spring arrangement of claim 1, wherein the mounting plate is connected to the node point of the spring member by welding.

4. The spring arrangement of claim 1, wherein the node point is located along a ridge line of the spring member.

5. The spring arrangement of claim 4, including a pair of slots (32, 34) located in the spring member close to the ridge line but on the opposite sides of the node point, wherein the slots extend longitudinally of the spring member.

\* \* \* \* \*